United States Patent
Levine et al.

(10) Patent No.: US 9,919,152 B2
(45) Date of Patent: Mar. 20, 2018

(54) CONDITIONAL GASTROINTESTINAL STIMULATION FOR IMPROVED MOTILITY

(71) Applicant: Enterastim, Inc., Newton, MA (US)

(72) Inventors: Andy H. Levine, Newton, MA (US); Michael Partsch, San Mateo, CA (US); Jay Pasricha, Ellicott City, MD (US); Jiande Chen, Clarksville, MD (US)

(73) Assignee: Enterastim, Inc., Newton, MA (US)

( * ) Notice: Subject to any disclaimer, the term of this patent is extended or adjusted under 35 U.S.C. 154(b) by 0 days.

(21) Appl. No.: 14/933,555

(22) Filed: Nov. 5, 2015

(65) Prior Publication Data
US 2016/0121111 A1 May 5, 2016

Related U.S. Application Data

(60) Provisional application No. 62/075,687, filed on Nov. 5, 2014.

(51) Int. Cl.
*A61N 1/36* (2006.01)
*A61B 5/0488* (2006.01)
(Continued)

(52) U.S. Cl.
CPC ...... *A61N 1/36007* (2013.01); *A61B 5/04884* (2013.01); *A61B 5/073* (2013.01);
(Continued)

(58) Field of Classification Search
CPC .......................... A61N 1/36007; A61N 1/0509
See application file for complete search history.

(56) References Cited

U.S. PATENT DOCUMENTS

| 4,801,294 | A |   | 1/1989 | Okada |
| 6,086,549 | A | * | 7/2000 | Neese ................... A61N 1/0524 |
|           |   |   |        | 600/554 |

(Continued)

FOREIGN PATENT DOCUMENTS

WO    2003/074123    9/2003

OTHER PUBLICATIONS

PCT International Search Report and Written Opinion issued in International Application No. PCT/US2015/059256 dated Jan. 13, 2016.

*Primary Examiner* — Tammie K Heller
(74) *Attorney, Agent, or Firm* — Greenberg Traurig, LLP; David J. Dykeman; Roman Fayerberg

(57) ABSTRACT

Systems and methods for gastrointestinal electrical stimulation to treat abnormalities in gastrointestinal motility are provided. In some embodiments, a system for relieving ileus includes an intraluminal catheter comprising: a catheter body having a proximal tip and a distal tip and a duodenal portion proximal to the distal tip of the catheter; and at least one electrode pair disposed along the duodenal portion of the intraluminal catheter, the at least one electrode pair being configured to detect a sensing information indicative of myoelectric activity of a patient and to provide stimulation energy; a sensing system in communication with the at least one electrode pair to receive the sensing information; and an energy delivery system in communication with the at least one electrode pair and the sensing system, the electrical energy delivery system being configured to delivery energy to the patient through the at least one second electrode pair based on the sensing information from the sensing system.

12 Claims, 14 Drawing Sheets

(51) Int. Cl.
  *A61B 5/07* (2006.01)
  *A61N 1/05* (2006.01)
  *A61N 1/372* (2006.01)
  *A61B 5/00* (2006.01)

(52) U.S. Cl.
  CPC .......... *A61N 1/0509* (2013.01); *A61B 5/4238* (2013.01); *A61B 5/4255* (2013.01); *A61B 5/6852* (2013.01); *A61B 5/6871* (2013.01); *A61B 5/6873* (2013.01); *A61N 1/37205* (2013.01); *A61N 1/37217* (2013.01)

(56) References Cited

U.S. PATENT DOCUMENTS

| | | |
|---|---|---|
| 7,430,450 B2 | 9/2008 | Imran |
| 7,444,183 B2 | 10/2008 | Knudson et al. |
| 7,734,340 B2 | 6/2010 | De Ridder |
| 7,742,795 B2 | 6/2010 | Stone et al. |
| 7,850,626 B2 | 12/2010 | Vaezy et al. |
| 7,941,221 B2 | 5/2011 | Foley |
| 8,371,701 B2 | 2/2013 | Ueda et al. |
| 8,485,980 B2 * | 7/2013 | Sinderby ............ A61B 5/0421 600/484 |
| 8,790,339 B2 | 7/2014 | Edwards et al. |
| 8,932,195 B2 | 1/2015 | Wieraszko |
| 8,983,627 B2 | 3/2015 | Pelger et al. |
| 9,427,580 B2 * | 8/2016 | Bork ................... A61N 1/0509 |
| 2002/0049395 A1 | 4/2002 | Thompson et al. |
| 2004/0162595 A1 | 8/2004 | Foley |
| 2004/0172088 A1 | 9/2004 | Knudson et al. |
| 2006/0079944 A1 | 4/2006 | Imran |
| 2006/0095008 A1 | 5/2006 | Lampropoulos et al. |
| 2006/0235286 A1 | 10/2006 | Stone et al. |
| 2008/0004484 A1 | 1/2008 | Wieraszko |
| 2008/0039715 A1 | 2/2008 | Wilson |
| 2008/0051656 A1 | 2/2008 | Vaezy et al. |
| 2009/0270963 A1 | 10/2009 | Pelger et al. |
| 2011/0029044 A1 | 2/2011 | Hyde et al. |
| 2012/0197251 A1 | 8/2012 | Edwards et al. |
| 2013/0006323 A1 * | 1/2013 | Tal ................... A61N 1/36007 607/40 |
| 2014/0330068 A1 | 11/2014 | Partsch et al. |

* cited by examiner

CONDITIONAL GASTROINTESTINAL STIMULATION FOR IMPROVED MOTILITY

RELATED APPLICATIONS

This application claims the benefit of and priority to U.S. Provisional Application Ser. No. 62/075,687, filed on Nov. 5, 2014, which is incorporated herein by reference in its entirety.

FIELD

The present disclosure relates to systems and methods for gastrointestinal electrical stimulation to treat abnormalities in gastrointestinal motility.

BACKGROUND

Gastrointestinal (GI) motility plays an important role in the health and well-being of persons of all ages. GI motility is one of the most critical physiological functions of the human gut. Without coordinated motility, digestion and absorption of dietary nutrients could not take place. To accomplish its functions effectively, the gut needs to generate not just simple contractions but contractions that are coordinated to produce transit of luminal contents (peristalsis). Thus, coordinated gastric contractions are necessary for the emptying of the stomach. Abnormalities in motility may lead to a variety of serious disorders, such as gastroparesis, Ileus, obesity, diarrhea, pseudo-intestinal obstruction, irritable bowel syndrome, and among many others. A need continues to exist for additional feasible and suitable means to treat GI motility disorders.

SUMMARY

The present disclosure provides systems and methods for gastrointestinal electrical stimulation to treat abnormalities in gastrointestinal motility.

In some aspects, there is provided a stimulation catheter that includes a catheter body having a proximal tip and a distal tip and a duodenal portion proximal to the distal tip of the catheter; and at least one electrode pair disposed along the duodenal portion of the intraluminal catheter, the at least one electrode pair being configured to detect a sensing information indicative of myoelectric activity of a patient and to provide stimulation energy. In some embodiments, the duodenal portion of the intraluminal catheter extends for between about 20 cm to 30 cm proximally from the distal tip of the catheter body. In some embodiments, the catheter may further include one or more pressure transducers disposed along the duodenal portion.

In some embodiments, the catheter includes at least one first electrode pair configured to detect the sensing information and at least one second electrode pair configured to provide stimulation energy. The at least one second electrode pair may be spaced apart from the at least one first electrode pair by a distance of between about 1 cm to about 10 cm. In some embodiments, multiple electrode pair spaced apart from one another may be provided to stimulate the bowel sequentially.

In some aspects, there is provided a system for relieving ileus that includes an intraluminal catheter comprising: a catheter body having a proximal tip and a distal tip and a duodenal portion proximal to the distal tip of the catheter; and at least one electrode pair disposed along the duodenal portion of the intraluminal catheter, the at least one electrode pair being configured to detect a sensing information indicative of myoelectric activity of a patient and to provide stimulation energy; a sensing system in communication with the at least one electrode pair to receive the sensing information; and an energy delivery system in communication with the at least one electrode pair and the sensing system, the electrical energy delivery system being configured to delivery energy to the patient through the at least one second electrode pair based on the sensing information from the sensing system.

In some embodiments, the energy delivery system is configured to deliver a single pulse of 100 msec at 4 mA in phase with natural electrical activity. In some embodiments, the energy delivery system is configured to deliver a pulse train of 20 hz at 1-10 mA in phase with natural electrical activity, with a pulse width of 2 msec and duration of 500 msec. In some embodiments, the energy delivery system is configured to deliver between 12 to 30 pulses per minute out of phase with natural electrical activity, the pulses being of 20 Hz at 4 mA, with a pulse width of 2 msec and duration of 500 msec.

In some aspects, there is provided a method for treatment of gastric motility issues that includes advancing an intraluminal catheter into a stomach of a patient, the intraluminal catheter comprising: a catheter body having a proximal tip and a distal tip and a duodenal portion proximal to the distal tip of the catheter; and at least one electrode pair disposed along the duodenal portion of the intraluminal catheter, the at least one electrode pair being configured to detect a sensing information indicative of myoelectric activity of a patient and to provide stimulation energy; positioning the duodenal portion of the intraluminal catheter in a duodenum of the patient; causing a sensing system in communication with the at least one first electrode pair to receive information from the at least one first electrode pair; and causing an energy delivery system in communication with the at least one second electrode pair and the sensing system to delivery energy to the patient through the at least one second electrode pair based on the sensing information from the sensing system. In some embodiments, the patient may be monitored to determine a type of motility the patient has, to determine whether to apply a synchronous electrical modulation if hypomotility is detected or to apply a inhibitory electrical modulation if uncoordinated hypermotility is detected.

In some aspects, there is provide a method for treatment of gastric motility issues that includes sensing information about motility of a patient from implanted at least one first electrode pair in a duodenum of a patient; determining a type of motility the patient has based on the sensed information; and based on the determined type of motility, communicating with at least one second electrode pair in the duodenum of the patient to deliver an electrical modulation energy to the patient, wherein a synchronous electrical modulation is applied if hypomotility is detected and an inhibitory electrical modulation is applied if uncoordinated hypermotility is detected. In some embodiments, the electrodes are contained within at least one capsule attached to a wall of duodenum. In some embodiments, such capsules include Bluetooth communication circuitry for communication with an external controller for sensing information.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

Figure 1:
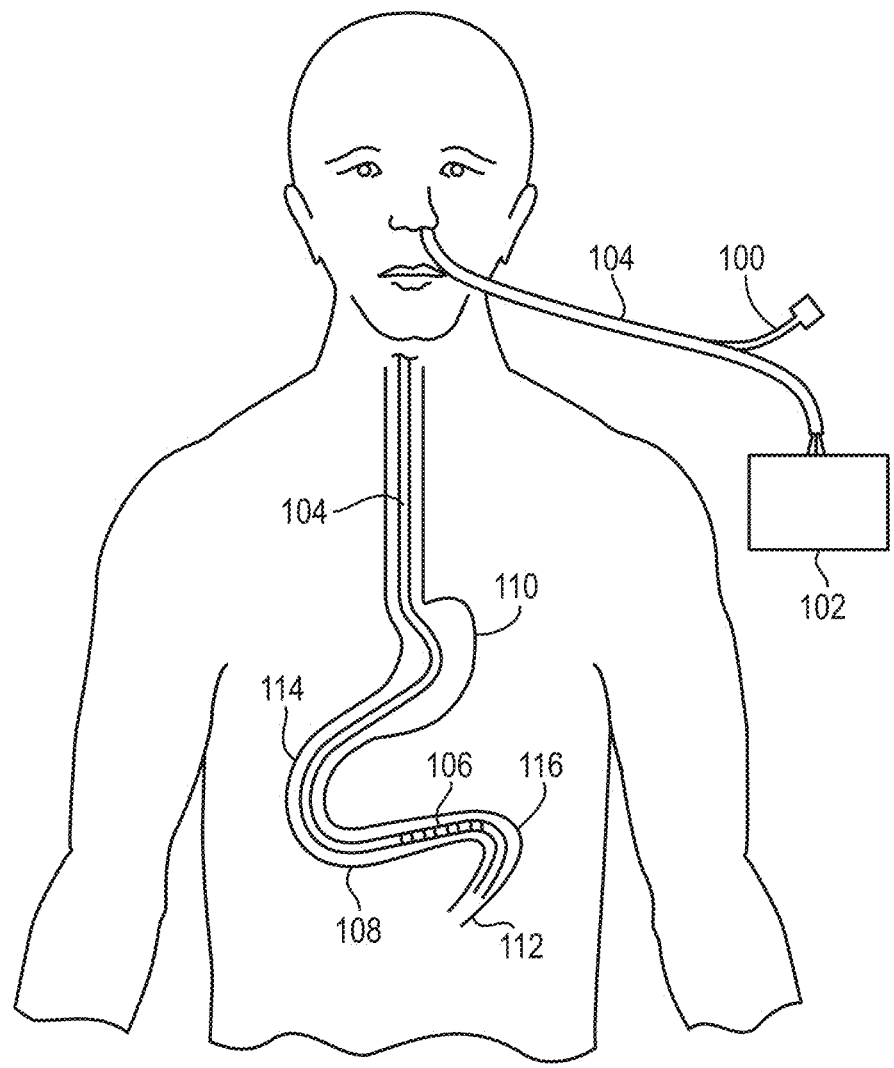
FIG. 1 schematically illustrates an embodiment of a system of the present disclosure in operation.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Systems and methods are described to provide stimulation to the stomach, small bowel (duodenum, jejunum, ileum) and the large bowel (colon) to enhance intestinal or gastric motility or other neurological responses and to enable patients with motility issues to take in nutrition orally or enterally (through a feeding tube). The systems and methods of the present disclosure may be used to treat motility issues caused by a variety of conditions, including, but not limited to, ileus, diarrhea, gastroparesis, short bowel syndrome, pseudo-intestinal obstruction, constipation or similar conditions. In some embodiments, the systems and methods of the present disclosure may be used to treat obesity, diarrhea, pseudo-intestinal obstruction, irritable bowel syndrome, ileus, gastroparesis, and constipation or for regulating appetite. Oral and enteral feeding may further stimulate normal motility of the GI tract. Stimulation is provided through an intra-luminal catheter connected outside the patient to a smart generator or via an implanted sensor/stimulator capsule attached to the bowel walls and either autonomously or remotely accessed. Uses include restarting of normal bowel motility following ileus caused by surgery, sepsis and other well-known causes of ileus and the prevention of ileus when used peri-operatively or immediately post-operatively. In some embodiments, the systems and methods of the present disclosure allow sequential pacing down the duodenum. In some embodiments, the systems and methods of the present disclosure allow stimulation of one location while relaxing or inhibiting an adjacent location.

When a patient presents with ileus, his or her symptoms may include nausea, bloating and vomiting which results in the inability of the patient to tolerate enteral feeding. Ileus typically occurs following abdominal surgery but may also occur as a result of trauma, infection, opioid use and many other causes. In some embodiments, a catheter is placed through either the nose or mouth, through the stomach and pylorus and into and through much of the duodenum, sometimes into the jejunum. Guidance of this catheter may be via visualization (endoscopic), radiologic, ultrasound, magnetic or other means. The catheter may include electrodes or electrode pairs that are used to sense the electrical activity of the duodenum and to subsequently provide electrical stimulation. The catheter may also include pressure transducers or channels for fluid to be connected to external pressure gauges. These pressure gauges may be used to monitor peristaltic activity of the GI tract more accurately than by electrical means, although electrical monitoring may be sufficient.

An initial monitoring period may be anywhere between 5 minutes and several hours (for example, 4 hours). In some embodiments, about 30 minutes may be used to determine if the cause of the ileus is a result of hypomotility, reduced or no contractions, or uncoordinated hypermotility, excessive and uncoordinated contractions. Using this information, the type of stimulation can be determined and delivered through the electrode pairs. Synchronous Electrical Modulation (SEM) may be provided if the ileus is caused from hypomotility. Inhibitory Electrical Modulation (IEM) may be provided if the ileus is caused from uncoordinated hypermotility. In some embodiments, SEM pulses are provided in synchronization with natural slow waves at a rate of up to 12 pulses per minute (ppm) in the duodenum, which corresponds to the natural frequency of slow waves in the duodenum. IEM is asynchronous and may be provided at a rate greater than the natural frequency or over 12 ppm in the duodenum, to interfere with natural contractility. This natural frequency of contraction varies from 3 ppm in the stomach to 12 ppm in the duodenum, 11 ppm in the jejunum and 8 ppm in the ileum.

In some embodiments, the initial stimulation may last between about 5 minutes and several hours (2 hours, for example). In some embodiments, after about 60 minutes of electrical stimulation, stimulation is stopped and natural activity is measured with either the electrodes and/or pressure gauges for about 5-120 minutes or about 30 minutes. If natural motility does not occur, the stimulation is repeated. Migrating Motor Complex (MMC) occurs roughly every 2 hours so this period of treatment may help to mimic natural activity. During the first or the second application of stimulation, liquid nutrition may be introduced through the stimulation catheter into the intestine. The presence of nutrition in the small bowel itself may have a stimulating effect on contractility. As the nutrition moves distally in the small bowel, it may enhance additional peristaltic response of the distal small bowel. The goal of this therapy is to permit oral or intestinal feeding without the need for the electrical stimulation.

In reference to FIG. 1, in some embodiments, the conditional gastrointestinal stimulation system of the present disclosure includes an introducer or delivery catheter, an intraluminal stimulation catheter 104 and an external controller 102.

A stimulation catheter 104 may be placed during the surgical procedure and the appropriate stimulation applied while the patient is undergoing surgery. By doing this, the intestine may be prevented from entering the ileus state which may speed recovery of the patient following surgery. The stimulation catheter 104 may also be placed through either a gastrostomy tube through the stomach wall to the small intestines or through a colostomy tube to the colon. In these cases, the catheter may be left in place to treat more chronic conditions such as gastroparesis and constipation. Typically, the catheter may be placed following the surgical procedure once the ileus is identified. A portable controller and battery pack may be carried for instance around the waist or may be suspended from an IV pole or a bed. The stimulation catheter 104 may be passed through the nose of the patient, through the esophagus, stomach, duodenum and sometimes into the jejunum 112.

The stimulation catheter 105 includes a plurality of electrodes 106 to be placed mainly in the duodenum. These electrodes 106 may connect proximally to a sensing and stimulation controller 102. The stimulation catheter may include a side branch 100 for injecting feeding solutions, withdrawing fluids and gasses and connecting pressure transducer lumens to readouts.

As shown in FIG. 1, when the stimulation catheter 104 is placed, the electrodes of the stimulation catheter 106 pass through the stomach 110 and reside in the duodenum 108. It may be beneficial to place this catheter completely through the duodenum 108 and into the jejunum 112, however, other placements are also possible. The duodenum is typically about 30 cm in length from the pylorus 114 to the ligament of Treitz 116 where the jejunum begins. Placing the catheter 104 beyond the ligament of Treitz may reduce the likelihood that the catheter is pulled back towards the stomach. In some embodiments, the catheter is sufficiently long to pass through the nose or mouth, the esophagus, the stomach, the duodenum and perhaps 10 cm into the jejunum. The overall catheter length may be about 150 cm to about 300 cm. In some embodiments, the catheter may be about 240 cm long. For chronic applications, the catheter could be placed through a PEG tube in the stomach wall. This would require a shorter catheter of between about 100 and about 200 cm or about 150 cm.

The catheter 104 may have at least two sets of electrodes 106 located between about 10 cm to about 30 cm from the pylorus, or at about 15 cm from the pylorus. As the distal end of the catheter would typically be located at the ligament of Treitz, which is about 30 cm from the pylorus, these electrodes may be located at about 10-20 cm from the distal end of the catheter. The catheter may have a bump or line located at between about 30 cm and about 35 cm from the distal end or, in some embodiments, at about 33 cm from the distal end. This bump or line can be used to align with the stomach side of the pylorus when the catheter 104 is in the proper position. In some embodiments, the portion of the catheter to be placed in duodenum (or duodenum portion) is between about 20 cm to 30 cm long. The duodenum portion may start at the distal terminal of the catheter or may be proximally set back by about 2 cm to 3 cm. In some embodiments, fluoroscopy may be used to visualize the electrodes to ensure they are about midway through the duodenum when in the proper placement. In some embodiments, the more proximal electrode pair may be used for sensing electrical activity of the duodenum, while the more distal pair may be used for passing electrical energy into the wall of the duodenum to stimulate the enteric nerves and/or smooth muscle. However, this configuration may be reversed.

In some embodiments, a single pair of electrodes can be used, which can electronically be switched from a sensing mode to a stimulating mode. In some embodiments, multiple pairs of electrodes for sensing and multiple pairs of electrodes for passing electrical energy. As noted above, in some embodiments, the proximal electrodes may be dedicated to sensing and the distal electrodes to stimulation, but such order may be reversed. In some embodiments, the electrodes may be positioned at about 10 to about 20 cm from the distal tip.

The electrodes of each electrode pair may be isolated from each other (bipolar). The electrodes may be made from platinum, iridium, stainless steel or other electrically conductive and biocompatible materials. In some embodiments, the electrodes may also be made from conductive and biocompatible wire that is wrapped around the circumference of the catheter multiple times. Wires are connected from each of the electrodes to the proximal end of the catheter which exits the patient.

Figure 8:
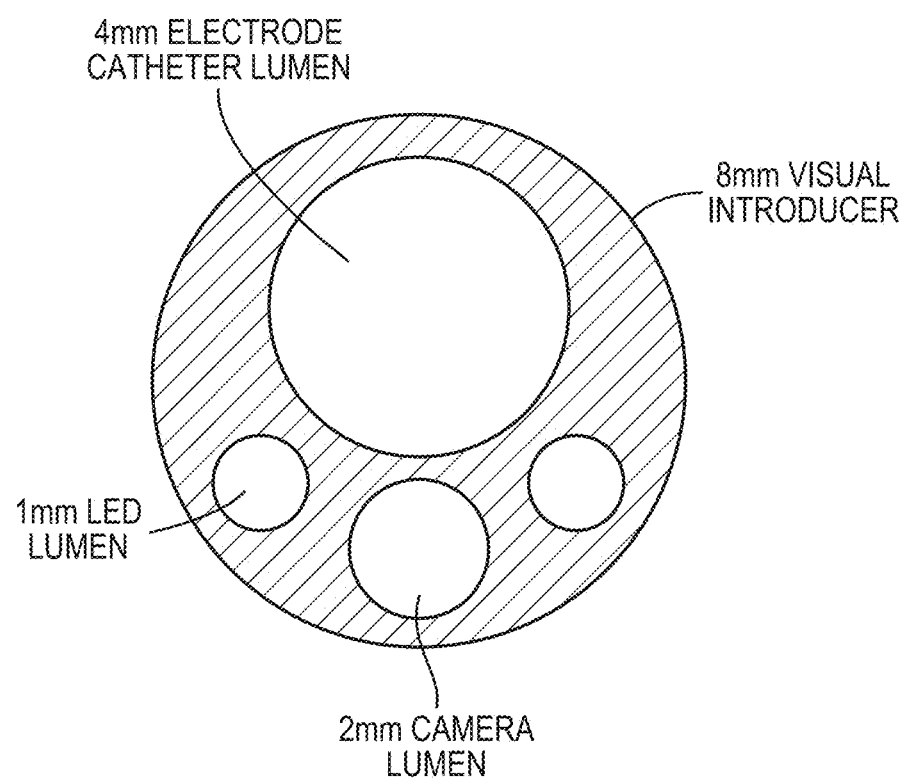
FIG. 8 illustrates a cross section of an introducer catheter of the present disclosure.

As shown in FIG. 8, in some embodiments, electrode wires are run through lumens in the catheter to connect electrodes to the sensing system and the energy delivery system. Multiple lumens may be extruded into the catheter for the electrode wires or the wires may be run through the central lumen. The electrodes may be mechanically, adhesively or thermally bonded to the catheter wall and exposed so that contact between the electrode and the bowel mucosa is ensured. The electrodes may be 2-7 mm in width or about 5 mm. Each electrode pair may be separated by a space of 3-15 mm or about 5 mm. Each set of electrodes may be separated by a space of about 1-10 cm or about 3 to 5 cm. More than one stimulation electrodes, for example, between 2 and 5, may be placed distal to the sensing electrodes on the catheter to better stimulate the bowel sequentially in a proximal to distal fashion to mimic peristaltic waves.

In some embodiments, the sensing electrode may be disposed between about 15 cm to 20 cm from the distal end of the catheter, and the stimulation electrodes may be disposed between about 3 cm and about 12 cm from the distal tip. In some embodiments, multiple stimulation electrodes may be disposed at about 12 cm, 9 cm, 6 cm and 3 cm from the distal tip of the catheter. In some embodiments, multiple sensing electrodes may be used, and such electrodes may be placed between the stimulation electrodes.

In some embodiments, additionally or alternatively to electrode pairs in the duodenum, one or two electrode pairs may be positioned at about 5 cm to about 10 cm proximal to the pylorus in the antrum or the greater curvature of the stomach. These electrodes can be used to sense and stimulate stomach contractions. In some embodiments, these electrodes may start at between about 38 cm and about 43 cm from the distal end of the catheter and progress proximally such that the stimulation electrodes would be between about 38 cm to 50 cm from the distal tip of the catheter and the sensing electrodes would be placed about 3 cm to about 10 cm proximal to the stimulation electrodes.

Figure 13:
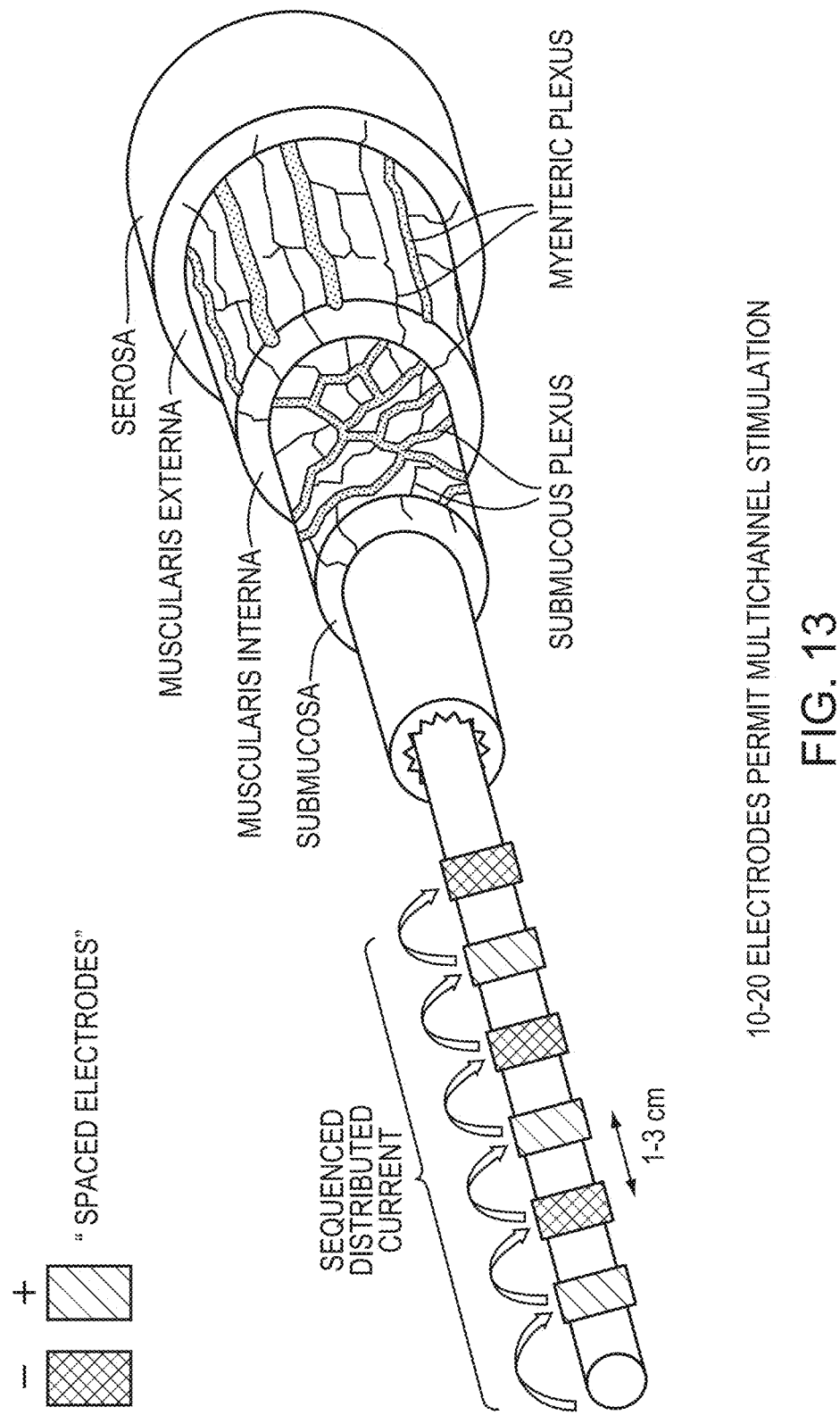
FIG. 13 illustrates an embodiment of a catheter of the present disclosure.

In some embodiments, as shown in FIG. 13, each electrode may be controlled separately from other electrode in electrode pairs. In some embodiments, electrodes are spaced evenly about 1 to 5 cm apart with between 10-20 electrodes down the length of the catheter such that all electrodes lie within the duodenum. In some embodiments, electrodes may start at about 10 cm to 15 cm from the distal tip and then be placed on the catheter every 1 cm to 2 cm. In some embodiments, such electrodes may be placed at about 15, 14, 13, 12, etc. cm from the distal end of the catheter. In some embodiments, these electrodes may be used as dual purpose electrodes, both for sensing and stimulation. With a series of electrodes, sequential stimulation of the duodenum may be performed by activating the electrodes from the proximal to the distal end, switching the polarity of each electrode as one goes distally.

Figure 14:
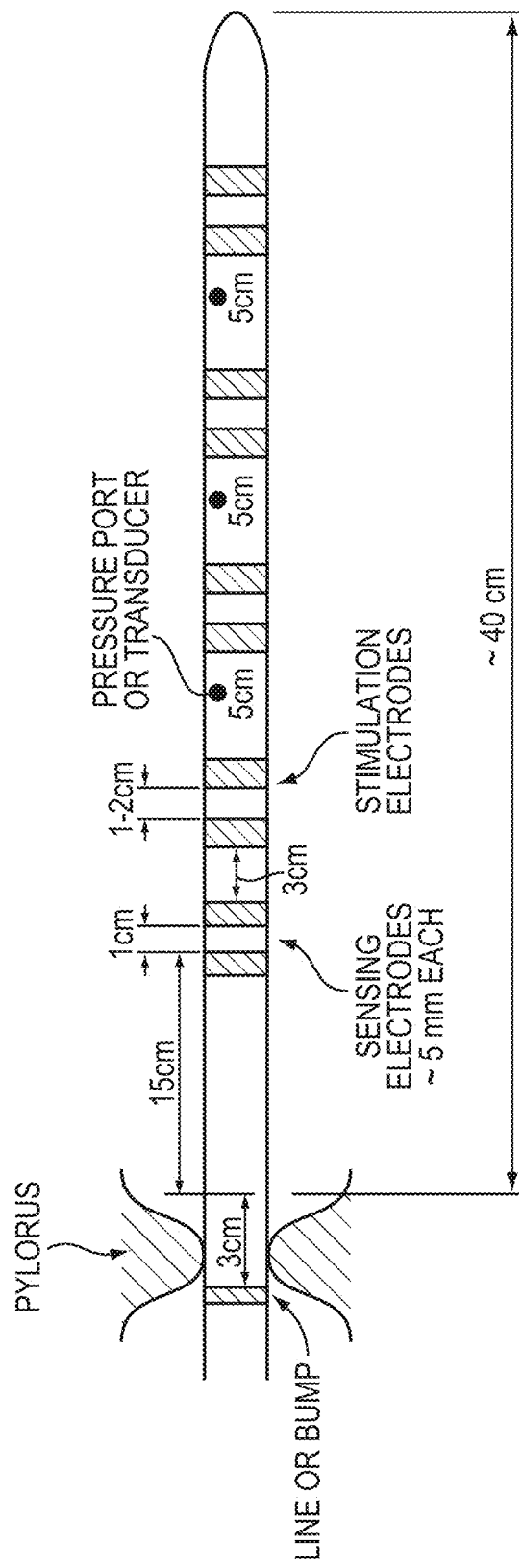
FIG. 14 illustrates an embodiment of a catheter of the present disclosure.

In some embodiments, as shown in FIG. 14, the catheter may be made slightly longer, by at least 40 cm, which would therefore be sufficiently long as to have its distal end at least 10 cm in the jejunum. The distal set of stimulation electrodes may be thus being in the jejunum.

Figure 4A:
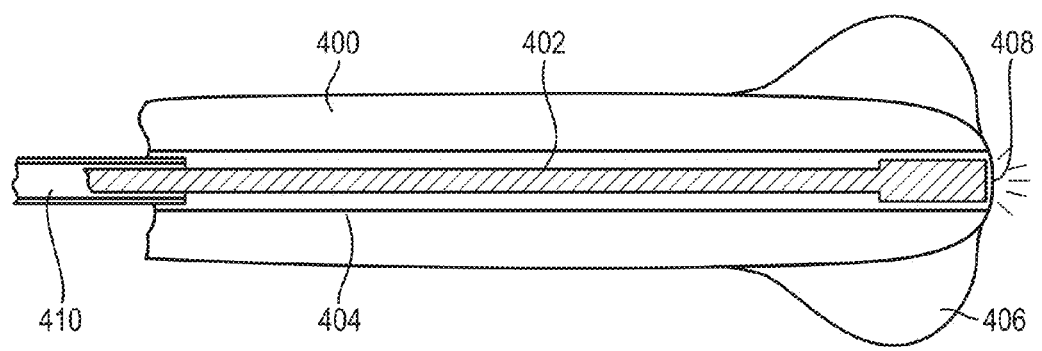
FIG. 4A illustrates an embodiment of a catheter of the present disclosure.

In reference to FIG. 4A, the catheter 400 may be sufficiently stiff to prevent its kinking or pulling back into the stomach, but may be sufficiently flexible to enable passage through the duodenum without trauma. The diameter of the catheter 400 may be about 5 mm (3-7 mm). The catheter may be fabricated from PVC, polyurethane, silicone or other biocompatible polymers. The catheter may have a central lumen 404 of about 2 mm (1-3 mm) diameter that runs the length of the catheter to its distal end. The central lumen may be used to either evacuate contents of the bowel or to deliver nutrition in the form of liquid nutrients to the bowel. Electrode wires may also be passed through the central lumen. In some embodiments, additional lumens may be provided for passage of the electrode wires to the proximal end or as pressure taps or the wires may be passed through the central lumen.

Figure 5:
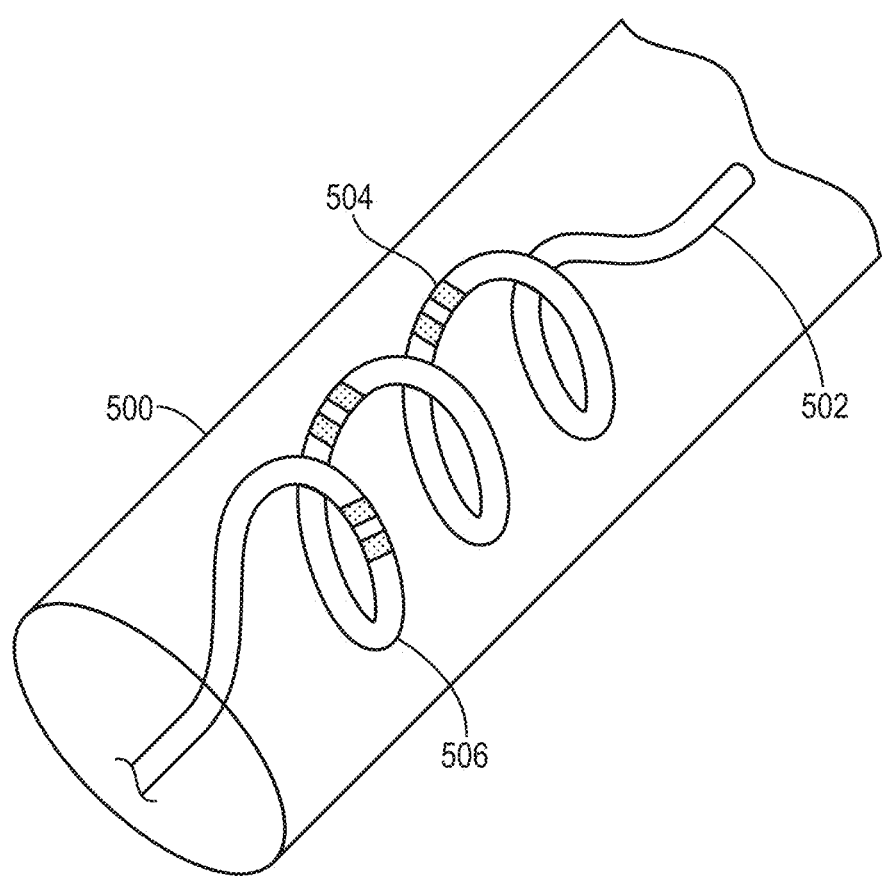
FIG. 5 illustrates an embodiment of a catheter of the present disclosure.

In some embodiments, the catheter is configured to ensure contact between the electrodes and the bowel mucosa to ensure transmission of stimulation and sensing electrical energy. In some embodiments, the catheter may be specifically shaped along its length to ensure contact between the bowel mucosa and the electrodes. For example, the catheter may have a spiral/corkscrew shape as shown in FIG. 5, S shape or a similar shape. In some embodiments, the shape could be thermally set into the catheter shaft if the catheter is made from a thermoplastic polymer such as urethane or nylon. In some embodiments, a wire with a pre-determined shape may be embedded or removal inserted into the catheter shaft, forcing the catheter to take the shape of the wire. The diameter of the spiral may be about 10 cm to about 25 mm for the small bowel and about 10 mm to about 50 mm for the large bowel. As shown in FIG. 5, catheter 502 may be placed in intestine 500 with multiple coils 506 causing electrodes 504 to engage the intestine wall.

Figure 2:
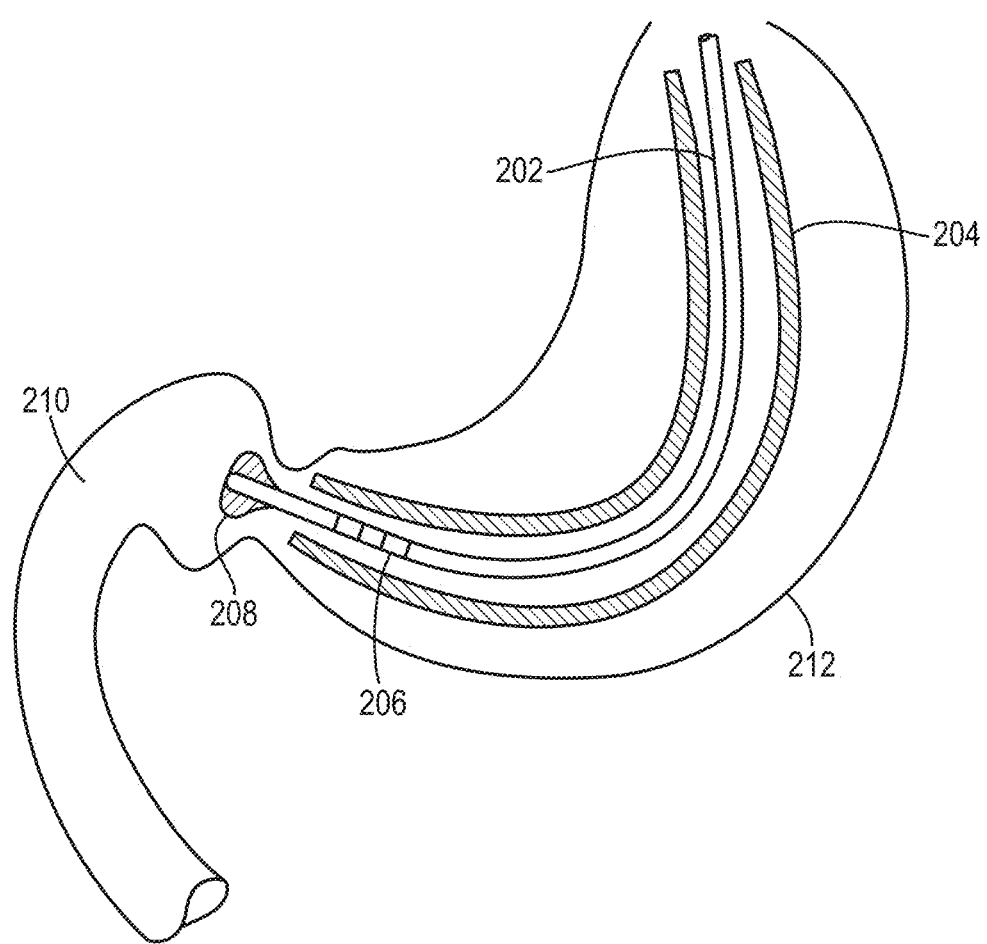
FIG. 2 illustrates a catheter of the present disclosure in the stomach of a patient.

FIG. 2 illustrates the catheter 202 having electrodes 206 in the stomach 212 as the catheter is being passed into the intestine 210. In some embodiments, to ease passage of the catheter 202 through the intestine 210, a ball or balloon 208 may be attached to the distal end of the catheter. If a balloon is used, the balloon may be inflated with water or air prior to advancing it through the bowel. The balloon or ball serves as an atraumatic bumper to resist perforation of the bowel. The balloon may have a minimal distal tip. The balloon may be made of a compliant material such as latex rubber, silicone or urethane, or may be non-compliant if made of stiffer materials such as PET. The balloon may be about 8-15 mm in diameter when inflated and may have a small profile upon collapse to allow the catheter to pass through any introducer catheters 204 that might be used to enable passage through the stomach. A lumen may be fabricated through the catheter to serve as an inflation lumen for the balloon. If a ball is used, the ball may also may be about 8-15 mm in diameter. The ball may be permanently attached to the distal end of the catheter, or may be remotely disengaged. The ball may be desired to make the distal ball from a radiopaque material such as titanium dioxide or barium filled plastics, to enable tracking with fluoroscopy or to embed a metal marker.

In some embodiments, one or more pressure measuring devices may be disposed at various locations along the length of the catheter. These pressure measurements may be used to detect the presence of peristalsis in the GI tract and may be located between electrodes or electrode pairs. Solid state pressure transducers such as those made by Millar (MikroCath) or MedKinetic (Ningbo China), strain gauge, piezoelectric or other transducers may be bonded to the catheter. In some embodiments, holes in the catheter may be cut or drilled that connect to lumens running the length of the catheter. These lumens may be filled with water and then connected to external pressure transducers. Pressure measurements may be desired at 1 to 20 locations along the length of the catheter. In some embodiments, 4 to 8 locations adjacent to the stimulation electrodes may be employed. If only 1 pressure transducer is used, it may be located at about 10-15 cm from the distal end of the catheter. It is also possible to monitor peristalsis with electrical activity alone thereby eliminating the pressure transducers.

The pressure measurement locations may be adjacent to the stimulation electrode pairs or mounted on top of the electrodes. If water manometry is used, the holes may also be used to infuse small amounts of nutrient solution when the electrode is in the SEM mode to synchronize peristalsis with feeding. The presence of nutrients in the small bowel may provide additional peristaltic stimulation. The ability to coordinate nutrient delivery at the contraction site may better achieve the ultimate goal of enhanced nutrition and improved peristalsis than current devices or than either therapy alone.

A hole in the catheter that connects with a lumen in the catheter may be located within the stomach to permit suctioning of food or gas from the stomach to keep the patient comfortable until peristalsis initiates. This hole may be located about 45-70 cm from the distal end of the catheter.

Introducer Catheter

In some embodiments, the introducer catheter system may be employed to permit easy and safe advancement of the stimulation catheter through the anatomy to the duodenum and jejunum. This may be done without any additional special instrumentation, but may also be assisted using image guidance devices such as ultrasound, fluoroscopy or endoscopic visualization. In placing feeding tubes, there is a risk that the tube is placed into the trachea instead of the esophagus. Also, placing feeding tubes past the pylorus can be difficult. The system described herein is intended to simplify placement.

Direct visualization may be used to enable the user to observe that the tube is in the correct lumen (esophagus). In reference to FIG. 4A and FIG. 4B, in some embodiments, a small endoscope 402 may be fabricated to pass through the central lumen 404 of the stimulation catheter. The endoscope may be either a fiber or electronic scope and may be 1-3 mm in diameter. If the endoscope is a chip type electronic camera with a lens and LED's used for light at its distal end 408, then wires may be routed through the central lumen of the stimulation catheter and connected to the external power source and a simple display unit. This endoscope may be reusable or disposable.

Figure 3:
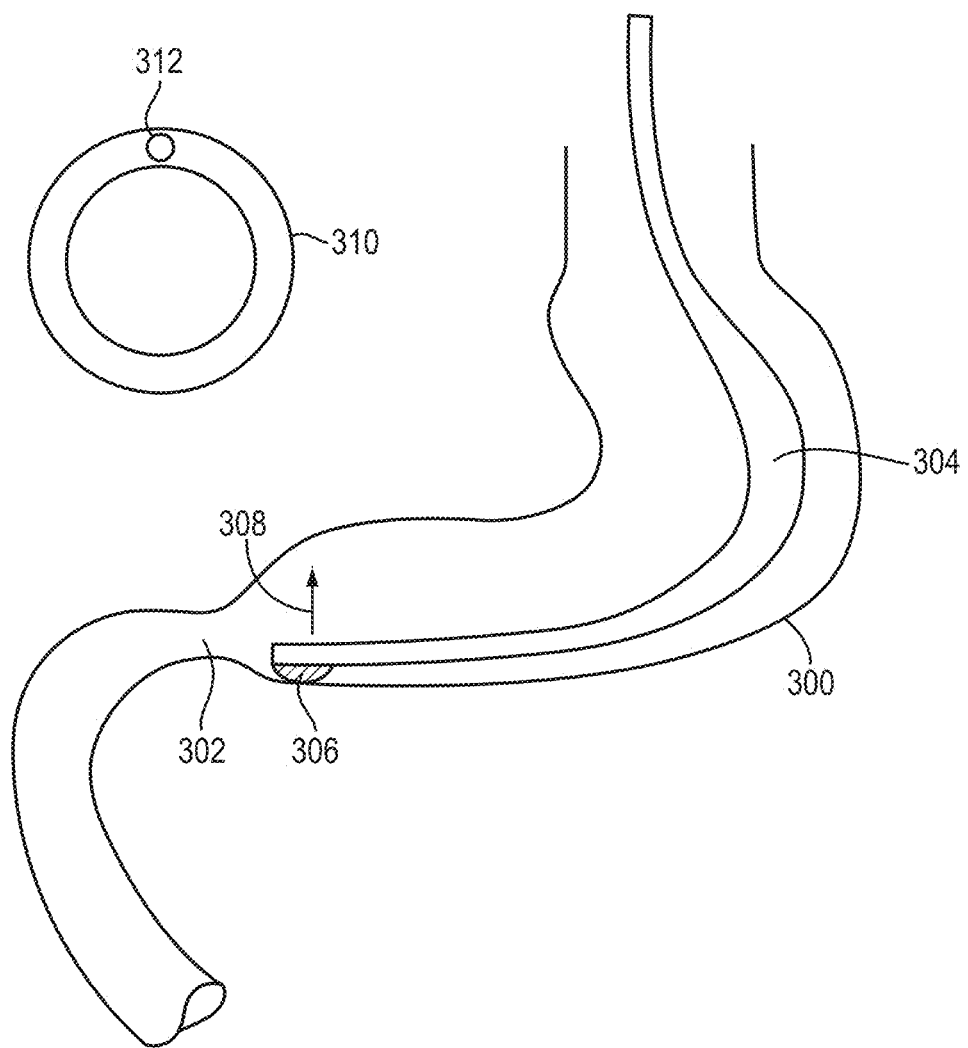
FIG. 3 illustrates a catheter of the present disclosure in the stomach of a patient.

In reference to FIG. 3, when introducing a catheter 304 into and through the stomach, the greater curvature of the stomach 300 may be used as a guide. A catheter may follow the greater curvature, which may guide the catheter towards the pylorus 302. To push the catheter through the pylorus, and to prevent kinking of the proximal shaft 304, among other benefits, a proximal portion of the catheter may be stiffened. This could be done by advancing a stiff metal or plastic core 410 down the inner lumen of the catheter, as shown in FIG. 4A. In some embodiments, an over sheath 204 may be advanced over the outside of the catheter 202 for the portion of the catheter that resides in the stomach 212, as shown in FIG. 2. In some embodiments, this stiff shaft or sheath may remain in the stomach 212, and would not be advanced through the pylorus.

An additional challenge can be to align the catheter 304 with the pylorus 302. Sometimes the catheter may hit the lower edge of the pylorus and not track through it. Deflection mechanisms may be built into the catheter such as off-center pull wires. In some embodiments, a wire may be run through a lumen 312 in extrusion 310 to the distal end of the catheter and attached at the distal end of the catheter with adhesive or other means. When this wire is pulled at its proximal end, it forces the distal end to curve towards the wire making the catheter steerable. Multiple lumens and wires around the catheter may be used for steering in multiple axes.

In some embodiments, a balloon 306 may be mounted to the distal end of the catheter, which may also be used to track through the duodenum, may be inflated in the stomach. This inflation may deflect the tip of the catheter 308 off the pyloric ledge and ease advancement into the pylorus.

Figure 4B:
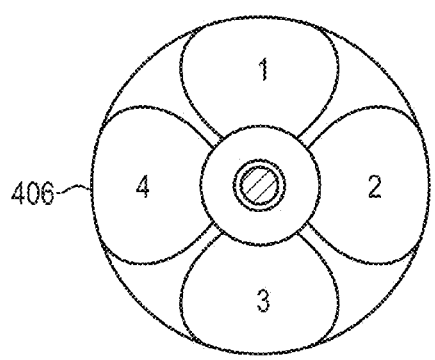
FIG. 4B illustrates an embodiment of a balloon suitable for use with a catheter of the present disclosure.

In some embodiments, as shown in FIG. 4A and FIG. 4B, a segmented balloon may be employed. Such segmented balloon 406 may be disposed around the catheter. In some embodiments, a balloon segment that is inflated can help push the catheter away from the stomach wall. By way of a non-limiting example, as shown in FIG. 4B, the segmented balloon 406 may have four segments 1-4, but more or less segments may be used. In some embodiments, only one segment may be inflated making the profile smaller for passage through the pylorus.

Figure 6:
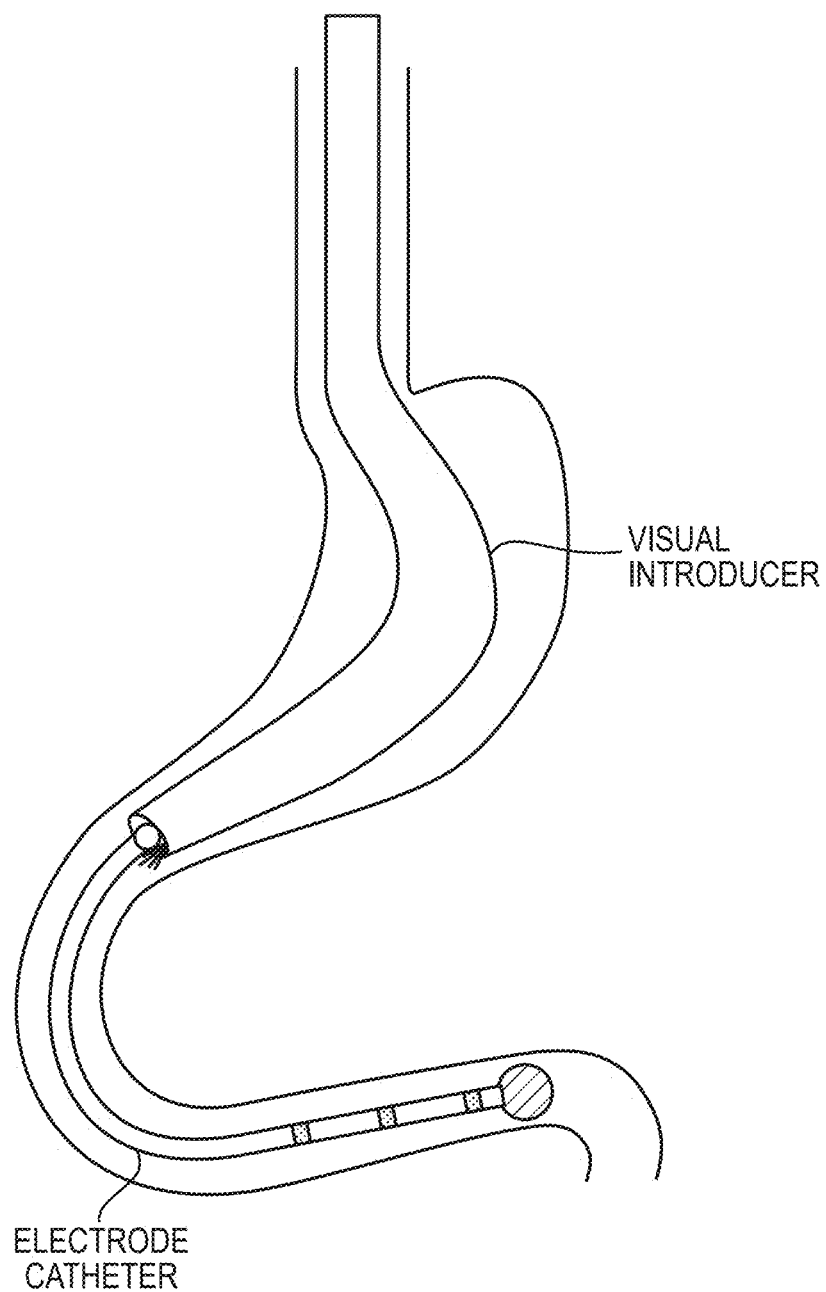
FIG. 6 illustrates an embodiment of an introducer catheter of the present disclosure.
Figure 7:
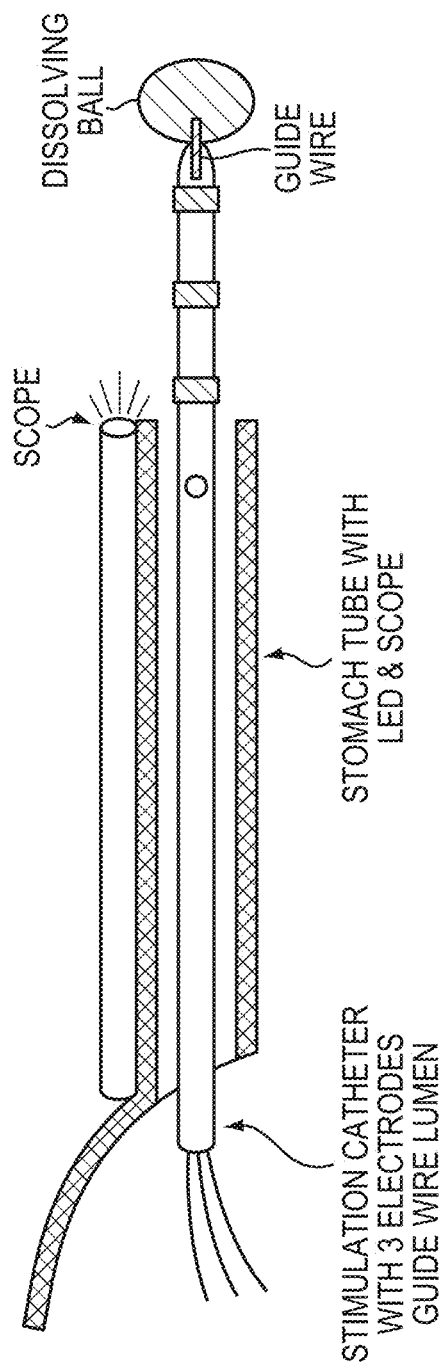
FIG. 7 illustrates an embodiment of an introducer catheter of the present disclosure.

Instead of or in addition to passing an endoscope through the central lumen of the stimulation catheter, as described above, visualization may be incorporated into the introducer catheter as shown in FIG. 6. The visual introducer may be first advanced through the esophagus into the stomach. The visualization can be used to ensure the tube is going through the esophagus and is positioned just at the pylorus. The stimulation catheter may then be introduced through the visual introducer, through the pylorus. Once in place in the duodenum, the visual introducer may be removed from the patient. This may be reusable or disposable. FIG. 7 shows the scope and light source passing through lumens in the wall of the visual introducer. An exemplary extrusion cross section is shown in FIG. 8 for this visual introducer device described in FIG. 7.

Stimulation Parameters

One of the goals of SEM is to generate contractions within the small intestine. In this method, each stimulus is synchronized with intrinsic myoelectrical activity. The SEM signals are believed to trigger the enteric nervous system to both contract and relax the small bowel. In some embodiments, the SEM parameters may be a single pulse of between about 50 msec to about 300 msec, in some embodiments, between about 75 msec and about 125 msec, at between about 1 and about 10 mA, in some embodiments, between about 4 mA and about 6 mA, in phase with natural electrical activity peaks or, if no activity is present, at 12 ppm (pulses per minute) in the duodenum.

In some embodiments, pulse trains may be used of between about 5 and about 100 hz, in some embodiments, between 15 hz and 25 hz, with a pulse width of between about 1 msec and about 15 msec, in some embodiments, between about 2 msec and about 4 msec, and duration of about 50 to about 500 msec, in some embodiments, between about 75 msec and about 125 msec. Such pulse trains may be delivered at about 1 mA and about 10 mA, and in some embodiments, between about 4 and about 6 mA.

In some embodiments, IEM may reduce the tone and tension of the small bowel to allow nutrients to pass through the small intestine with reduced resistance. This may be accomplished by stimulating the bowel out of phase with natural myoelectrical activity by stimulating at over 12 ppm (in the duodenum) at between about 15 ppm and about 30 ppm, in some embodiments, between about 18 ppm and 22 ppm, with parameters similar to those described above.

If there is one electrode pair on the catheter, then it is stimulated per above. If multiple pairs of electrodes are present, the may be stimulated from the proximal to the distal end in sequence with a phase shift (time delay between electrode pairs) that is present under normal conditions. In some embodiments, cycles of both SEM and IEM may be incorporated simultaneously in differing portions of the intestine. For example, when a proximal stimulation electrode pair is in SEM, a more distal electrode pair may be in an IEM mode, or vice versa. In some embodiments, both gastric excitation (SEM) and inhibition (IEM) may be incorporated with coordination such that the duodenum is activated when the stomach is inhibited and vice versa.

External Controller

The external controller takes input from the pressure sensors and/or electrical sensors and determines what type of contractile pattern is present. In some embodiments, this is done via peak detection. If hypomotility is detected, then the appropriate SEM signal is sent to the stimulation electrodes. If multiple electrodes are used, then stimulation occurs from the proximal to the distal electrode.

System for Delivery of Intestinal Stimulation

Figure 9:
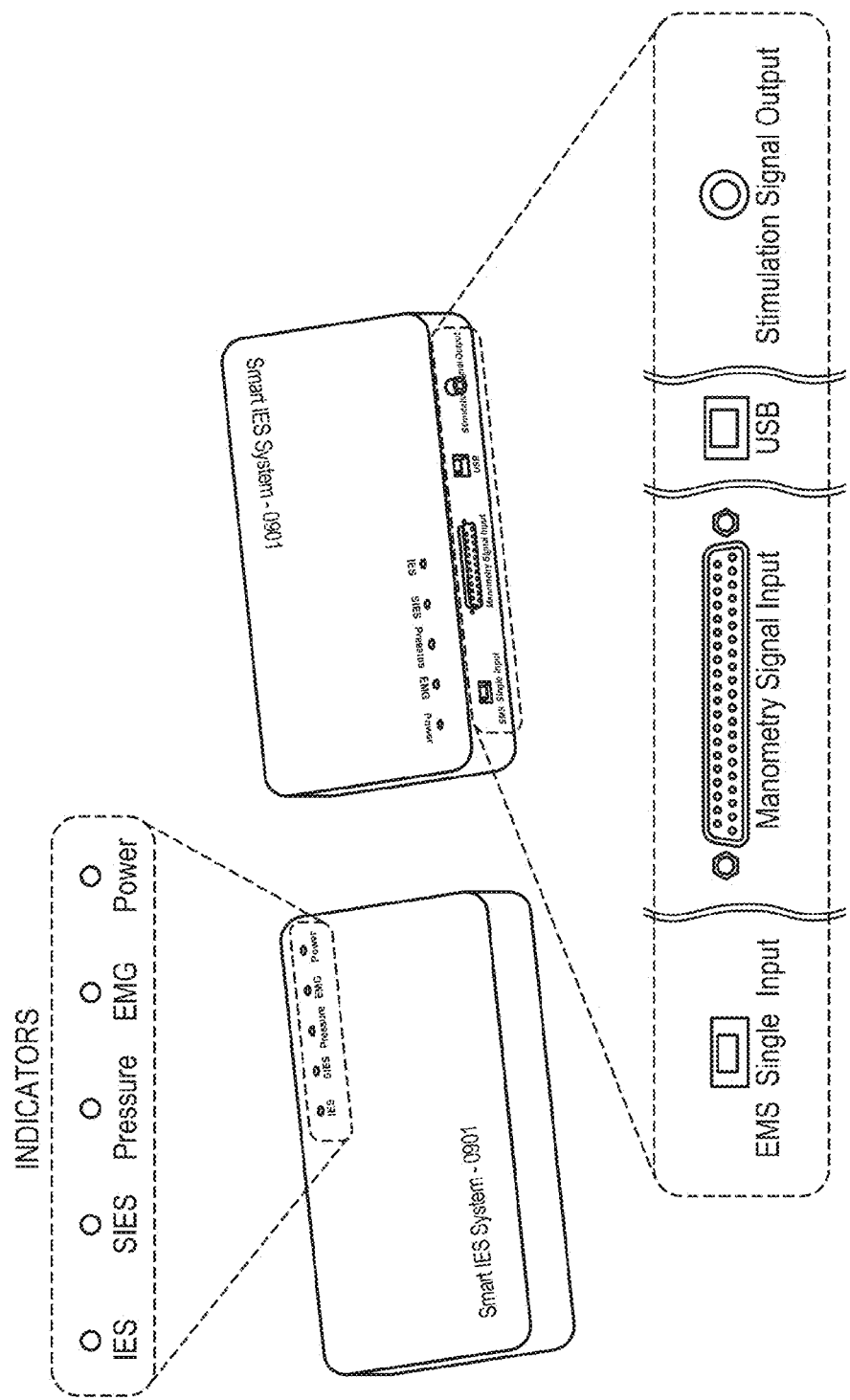
FIG. 9 illustrates an embodiment of an intestinal electrical stimulation device of the present disclosure.

The entire system may be composed of an intraluminal catheter (i.e. stimulation catheter as described above), an intestinal electrical stimulation (IES) device and a personal computer (PC). FIG. 9 illustrates an embodiment of an IES device. The IES device may be configured to receive and amplify contractile (pressure) and myoelectrical signals from a patient via the stimulation catheter, communicate with the PC (control unit) to determine the mode and pattern of (IES) and deliver the stimulation to the small intestine of the patient via the stimulation catheter. During the treatment, the stimulation catheter may be placed into the proximal small intestine to deliver IES to the small intestine. Intestinal contractions can be measured by the system and displaced on the PC.

Figure 10:
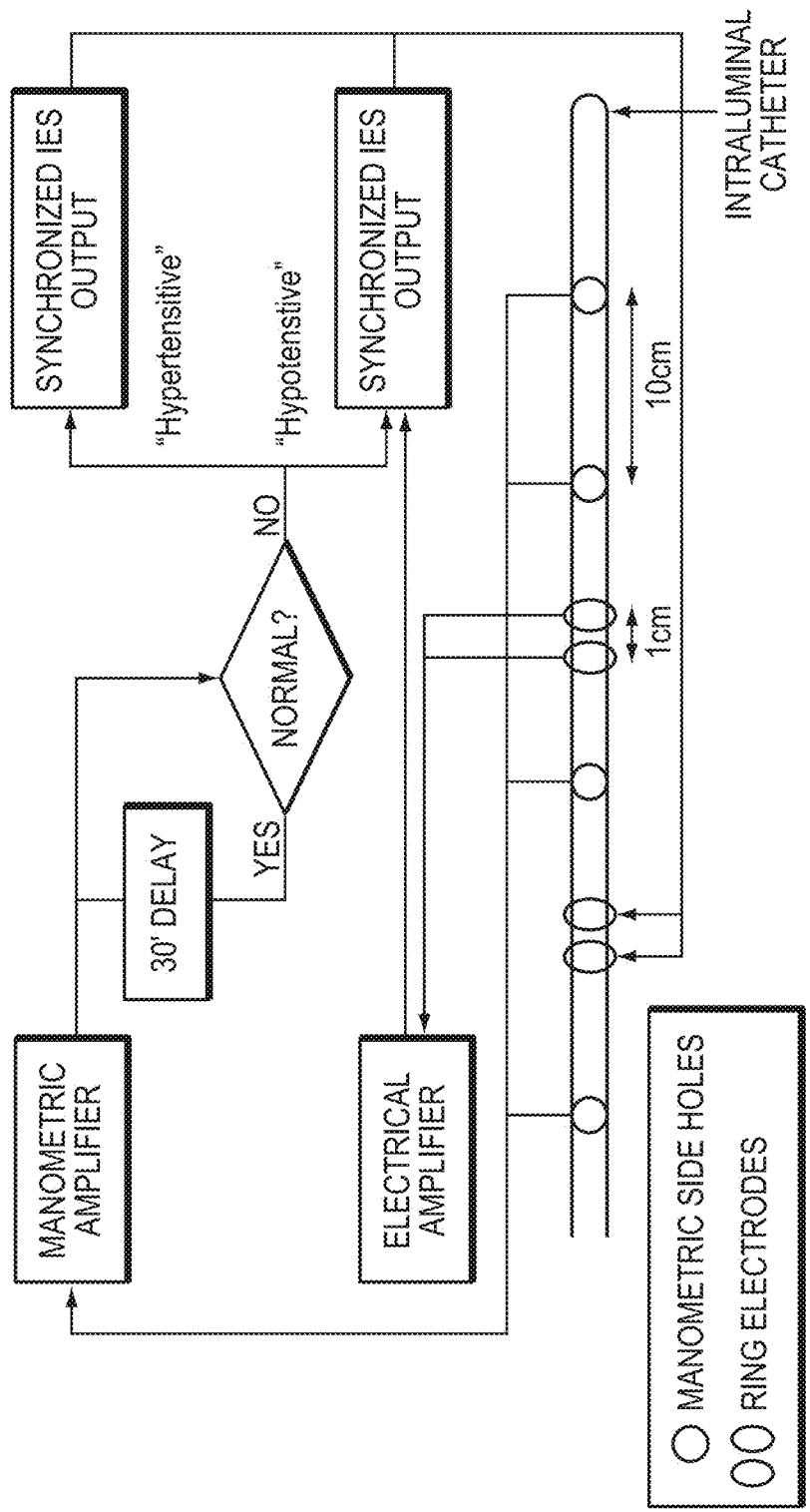
FIG. 10 is a flow chart for determining an output mode of a stimulator of the present disclosure.

In reference to FIG. 10, the output mode of the stimulator can be determined as follows:

a. If the recorded intestinal contractions during the past 30 min (or any other desired time period) are normal, EM does not need to be performed.

b. If intestinal contractions are hypotensive (myopathy), SEM may be delivered, i.e., each electrical stimulus may be delivered at the detection of an intestinal slow wave peak (measured by the EMG amplifier).

c. If intestinal contractions are hypertensive and uncoordinated (neuropathy), IEM may be performed with parameters known to inhibit intestinal contractions.

Whether EM is delivered or not, the intestinal contraction may be continuously measured and their pattern may be assessed every 10 minutes (or any other desired time period) and a new decision for SEM or IEM or no stimulation is made.

Functionally, the IES system can be classified into measurement, control and stimulation units. In some embodiments, the measurement unit may include an EMG amplifier and a manometric system; the control unit may include a PC and data transmission among different modules; and the stimulation unit may be configured to deliver specific electrical pulse.

Manometric System: In some embodiments, the IES system may include a multi-channel manometric recording unit depending on the number of pressure transducers located on the catheter. This unit is used to record intestinal contractions of a patient. In some embodiments, as described above, the stimulation catheter may include side holes and a water perfusion system and an amplifier. In some embodiments, solid state pressure sensors may be placed on the catheter. In some embodiments, a manometric system may be incorporated in the stimulation catheter.

EMG amplifier: The EMG amplifier may be used to amplify intestinal myoelectrical activity. In some embodiments, a stand-alone 4 channel EMG amplifier can be used. In some embodiments, a one channel EMG amplifier can be integrated into the IES device. The recorded intestinal myoelectrical activity (slow waves) can be used to trigger stimulation when SIES mode is selected.

Control unit. The unit may be composed of a PC and data transmission, and is used to control the mode of IES. Some functions of the control and data transmission unit are as follows: a) to facilitate data transmission among different modules in the device via internal high speed data bus. For example, this unit can take measurement data from the manometric and EMG amplifiers and temporarily store them in the memory during the analysis process, and send these data to the PC for display and permanent storage; b) to analyze the intestinal contractile data using the algorithm obtained from the PC and to determine the pattern of intestinal motility; c) to determine the output mode of the stimulator according to the pattern of intestinal motility; and d) to detect the peak of each intestinal slow wave and use it to trigger the output of the stimulator when the stimulator is working in the mode of synchronized IES.

Several algorithms can be developed and stored on the PC, including the followings 1) software for the analysis of intestinal contractions; 2) algorithm for the selection of IES mode; 3) algorithm for detection of slow wave peak.

Stimulation unit (pulse generator): The stimulation unit may be used to perform inhibitory IES (IIES) or synchronized IES (SIES). A micro-stimulator may be used to generate universal wave forms, including pulse trains that will be used for EM. In the mode of SEM, each stimulus output can be triggered by the detection of each intestinal slow wave peak. By way of a non-limiting example, the following parameters may be used: train on-time of 0.5 s, off-time of 1.5 s, frequency of 20 Hz, pulse width of 2 ms and amplitude of 4 mA. The stimulation unit can be designed to have the following capacities: train on- and off-time of 0-10 min, frequency from 0.05 Hz to 200 Hz, pulse width from 10 µs to 600 ms (depending on frequency) and amplitude up to 20 mA.

Remote Stimulation

Figure 11:
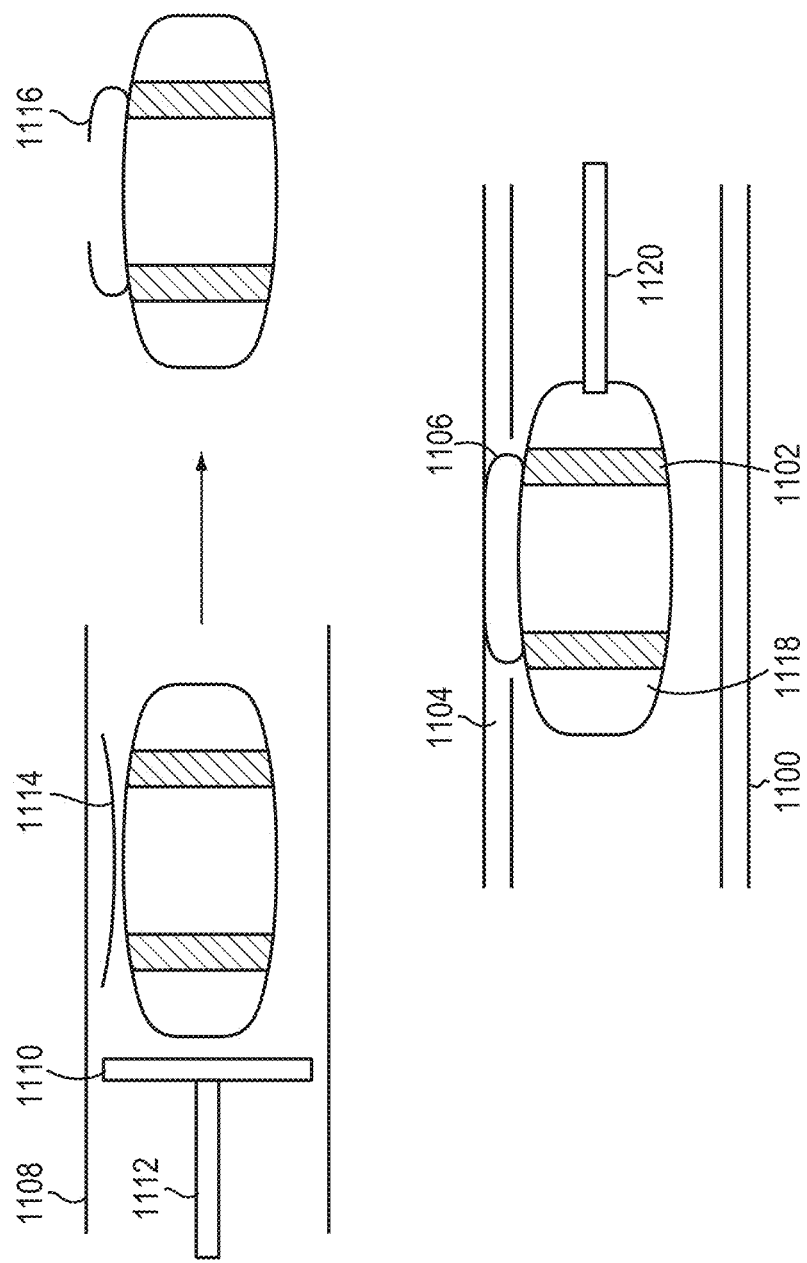
FIG. 11 illustrates an embodiment of a stimulation system of the present disclosure.

In reference to FIG. 11, in some embodiments, systems and methods are provided for stimulating the intestine 1100 with a remote system. The sensor/stimulator capsule 1118 may be attached to the wall of the intestine 1100 using various mechanical means, such as staples 1106. In some embodiments, a coil could be screwed into the tissue or a barb could be advanced into the tissue. In some embodiments, the sensor/stimulator capsule 1118 can be embedded into tissue 1104 of the intestine 1100 or adhesively bonded to the mucosa or submucosa. The sensor/stimulator capsule 1118 may be delivered through a catheter 1108 with a pusher mechanism 1112 and plate 1110. The sensor/stimulator capsule 1118 may be loaded into the catheter which is advanced into the intestine as described above. This may be done during surgery. When located in the desired position in the intestine, the pusher is advanced, pushing the sensor/stimulator capsule 1118 from the catheter. The attachment means, in this case staples 1114, are loaded such that they are flat when inside the catheter. They may be made of Nitinol metal and pre-shaped as shown in 1116. These attachment means may be staple or hook-like taking advantage of either the superelastic or shape memory properties of Nitinol. As the sensor/stimulator capsule 1118 is pushed distally out of the catheter, the staples form and grasp the intestine wall. This attachment is likely to be good for 5-30 days, after which the intestines will push the device out and it will pass through the GI tract normally and be excreted. Errodable polylactic acid, or equivalent polymeric attachment means between the anchors 1116 and the capsule 1118 may enhance control over attachment duration. In some embodiments, the entire attachment barb or staple could be made of a biocompatible erodible or resorbable material permitting timed release. In some embodiments, the barbs could be retracted by a mechanical device such as a motor and screw mechanism in the sensor/stimulator capsule 1118 thus releasing the attachment. In some embodiments, tissue adhesive could be used in patches to secure the sensor/stimulator capsule 1118 to the lumen wall or could be excreted by the sensor/stimulator capsule 1118 at the appropriate location. The sensor/stimulator capsule 1118 may also be delivered manually during surgery through the stomach or intestine. The sensor/stimulator capsule 1118 may also be used in the colon to treat constipation.

The electrodes 1102 contact the mucosal tissue 1104. These electrodes may measure the electric potential with respect to ground or to the other electrode(s) on the device. They therefore receive electrical signals from the intestine such that the natural electrical activity is measured. These signals are analyzed in the capsule 1118 with internal circuits to determine the optimal stimulation parameters needed to stimulate peristalsis. The same, or other, electrodes 1102 are then used to provide electrical energy (under voltage or current control) to the wall of the intestine to provide the appropriate stimulations to cause peristalsis. The stimulation waveforms are typically pulsatile, bipolar, charge-balanced waveforms, but could be unipolar and not charge-balanced if hyperpolarization (inhibition) is desired. Waveforms may be delivered in a pulsatile fashion.

In some embodiments, the circuit may be controlled by an external controller which is coupled to the sensor/stimulator capsule 1118 by RF with a coil placed on the outside of the patient's abdomen. The sensor/stimulator capsule 1118 may have a tail 1120 on either or both sides of the capsule which may serve as an antenna to transmit data on peristaltic activity to a receiver outside the body. For data transmission, the capsule may contain an integrated circuit that contains a Bluetooth®, low energy, "system-on-a-chip" connected to the antenna. Alternatively, radio frequency chips and antennae may also be used. For energy transmission from the outside to the inside of the body, the capsule may contain an inductive charging coil and charging circuitry which is inductively matched to an external coil placed against the skin.

In some embodiments, the barbs in the duodenum may be deployed by covering the sensor/stimulator capsule 1118 and barbs in a material that dissolves at elevated pH such that the prongs or barbs are held normally flat. This sensor/stimulator capsule 1118 may be ingested prior to surgery. Upon reaching the elevated pH of the duodenum, the coating may dissolve and the prongs exposed to the duodenal wall thereby engaging the wall. Coatings may include methyl acrylate, cellulose, alginate and other polymers. In some embodiments, a pH sensor may be incorporated into the sensor/stimulator capsule 1118. Upon measuring elevated pH, the pH sensor could activate a motor to screw a corkscrew into the intestine or it could activate a heating circuit that would heat a shape memory metal holder to release the barbs.

The sensor/stimulator capsule 1118 may contain batteries, at least 2 electrodes and a circuit board with both active and passive components. The circuit board could contain a microprocessor or dedicated circuit to perform signal processing and stimulation. Upon deployment in the duodenum, the sensor/stimulator capsule 1118 may sense the myoelectric activity and trigger pulses as needed. It may also transmit data outside the body.

Communication with the sensor/stimulator capsule 1118 from the outside of the body may be made to measure pH, myoelectrical activity, pressure from a solid state pressure transducer. Also, communication may be made from the outside to the sensor/stimulator capsule 1118 to have it deploy anchors at specific time or location, release anchors, start or stop stimulation.

Pattern of EM:

In some embodiments, alternating excitatory and inhibitory currents can be applied in a progressive manner so that in effect peristalsis is simulated. This may also induce the same impact in the adjacent small bowel. In some embodiments, bolus feeds may be applied and synchronized in between the rings to coincide with "propulsive" currents.

In some embodiments, the pulse width of the stimulation used is greater than most neural stimulation waveforms. This may aid in stimulation of both the enteric nerves and the smooth muscle in the intestinal wall. For example, while the typical nerve stimulation waveforms have a pulse width of microseconds, in some embodiments of the present disclosure the pulse width is 50-300 msec.

Figure 12B:
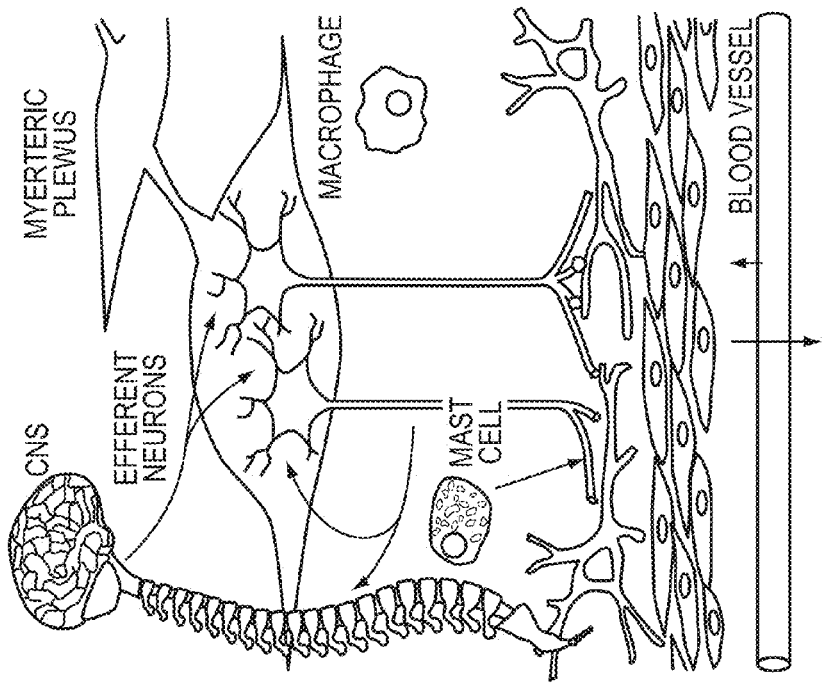
FIG. 12A, FIG. 12B, and FIG. 12C present a schematic representation of operation of the gastrointestinal track.
Figure 12A:
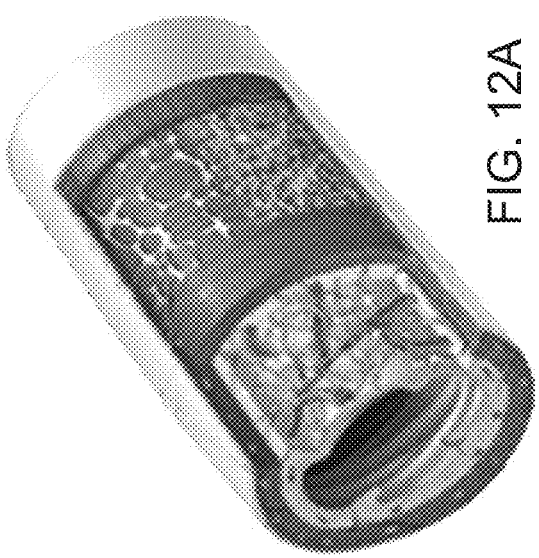
Figure 12C:
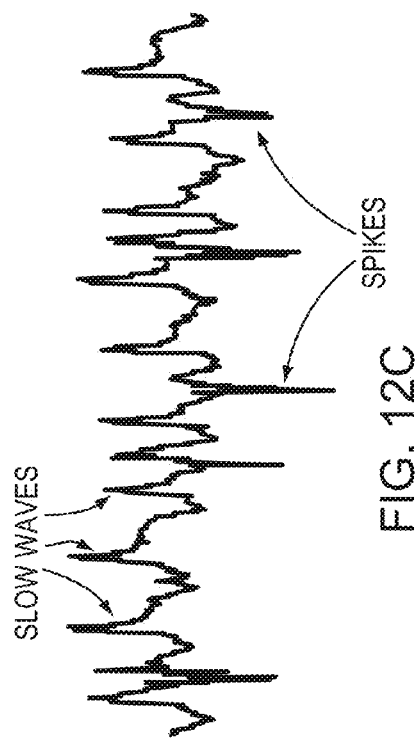

In reference to FIG. 12A, FIG. 12B and FIG. 12C, movement of food through the GI tract is controlled by several complex neural and hormonal mechanisms. These control mechanisms are both local and systemic in their expanse. The enteric nervous system which runs the length of the GI tract is said to be our second brain. The Interstitial cells of Cajal (ICC) serve as electrical pacemakers in the intestines and create the bioelectrical slow wave potential that leads to contraction of the smooth muscle. Electrical slow waves spread from ICC to smooth muscle cells and the resulting depolarization initiates calcium ion entry and contractions. Slow waves organize gut contractions into phasic contractions that are the basis for peristalsis. Spike electrical potentials superimpose on slow waves and correspond to muscle contractions. Small intestine slow waves originate from the proximal duodenum and propagate as an annular wave front distally.

Although the exact causes of ileus are not known, ingestion of opioids and inflammation and resulting disruption of enteric nerve stimulation have been implicated. This can take the shape of reduced slow waves, reduced spikes or uncoordinated slow waves. Therefore, stimulating the enteric nerves directly with an intraluminal catheter as disclosed herein is likely to overcome local pathology and reset normal peristalsis.

In some embodiments, using a wider pulse may be useful to stimulate a wider area. This may allow impacting a defect regardless of whether the defect is the enteric nerves or the smooth muscle cells.

In some embodiments, the nerve stimulation as described herein may be used to reduce inflammation, which may in turn cause the ileus. One mechanism of achieving this is through the inhibition of the sympathetic nerve activity and IL6 activity.

In the ICU setting, ileus may be more complex than in the post-operative (POI) setting. ICU patients may have more problems that could impact ileus including sepsis. In POI, the combination of electrical stimulation and concurrent feeding should have a rapid impact on reversing ileus. In the ICU, the stimulation catheter may be left in longer, perhaps days, maintaining stimulation and feeding until the underlying problem resolves.

EXAMPLES

The following non-limiting examples of the systems and methods of the present disclosure are merely representative and should not be used to limit the scope of the present disclosure. Large varieties of alternative designs exist for the systems and methods and are within the spirit and the scope of the present disclosure. The selected examples are therefore used mostly to demonstrate the principles of the methods and devices disclosed herein.

Example 1

Intraluminal Intestinal Electrical Modulation can Completely Entrain Intestinal Slow Waves in Dogs Aim: To investigate the feasibility of intraluminal intestinal stimulation and compare the effects to serosal stimulation.

Methods: Nine healthy hound dogs were used for this experiment. Four pairs of electrodes were implanted on the serosa of the jejunum at an interval of 5 cm with the most proximal pair 35 cm beyond the pylorus. An intestinal fistula was made 20 cm beyond the pylorus. Following recovery, simultaneous recordings of intestinal myoelectrical activity were made for 2 hrs in the fasting state from both intraluminal and serosal electrodes. Various electrical stimulation parameters were tested.

Results: The frequency of the intestinal slow wave recorded from the intraluminal electrodes was identical to that from the serosal electrodes 18.7±0.3 cycles/min vs. 18.7±0.3 cpm ($r=0.99$, $p<0.001$), as was the percentage of normal 17-22 cpm waves (95.8±3.9% vs. 98.1±1.33%, ($r=0.96$, $p<0.01$). Complete entrainment of intestinal slow waves was achieved in every dog with IES using intraluminal ring electrodes. The effective stimulation parameters were pulse width of 70 ms, amplitude of 4 mA and frequency of 1.1×IF.

Example 2

Synchronized IES Stimulates Intestinal Motility and Accelerates Transit in Dogs in a Hypomotility Model Aim: To investigate effects of synchronized IES (SIES) on small intestinal motility in dogs.

Methods: Seventeen dogs were equipped with a duodenal cannula for the measurement of small bowel motility using manometry. An additional cannula was placed in six of the dogs at 1.5 m distal to the first one for the measurement of intestinal transit. Two pairs of bipolar electrodes were implanted on the proximal intestine; one for stimulation and the other for recording slow waves. Glucagon ($2.87 \times 10^{-2}$ µmol/kg) was used to induce postprandial hypomotility. Pulse trains were used for SIES with the following parameters: train on-time of 0.5 s, pulse frequency of 20 Hz, pulse width of 2 ms and amplitude of 4 mA and each train of pulses was delivered at the detection of intestinal slow wave peak.

Results: 1) SIES induced small intestinal contractions during phase I of the migrating motor complex. (Contractile index or CI: 5.2±0.6 at baseline vs. 10.3±0.7 with SIES, P=0.003) 2). In the fed state, SIES significantly improved glucagon-induced hypomotility (CI: 3.4±0.5 vs. 6.0±0.3, P=0.03) 3). SIES significantly accelerated small intestinal transit delayed by glucagon (70.4±3.1 min vs. 44.5±3.1 min, P<0.01). 4). There was a negative correlation between the contractile index and transit time (r=−0.427, p=0.048). 5) The excitatory effect of SIES was blocked by atropine. 6) Similar enhancement was noted with SIES using intraluminal electrodes.

Example 3

IES Stimulates Intestinal Motility and Accelerates Transit in Dogs in a Disordered Motility Model Aim: To study the effects of serosal and intraluminal IES on postprandial small intestine contractions in a model of dysmotility.

Methods: This experiment was performed in six dogs implanted with dual cannulas in the small intestine with an interval of 150 cm. A nitric oxide synthesis inhibitor, nitro-L-arginine (L-NNA) was used to induce disordered and spastic (hypertensive) intestinal motility. The study consisted of four randomized sessions on separate days with an interval of at least 2 days: session 1 (L-NNA), session 2 (L-NNA plus serosal IES), session 3 (L-NNA plus intraluminal IES) and session 4 (control session), In the L-NNA session, after an overnight fast each dog was fed with 237 ml liquid. Then L-NNA (5 mg/kg) in 20 ml saline was infused intravenously for 20 min. Small bowel contractions were measured during the entire session using a manometric system. Sessions 2 and 3 were the same as the L-NNA session except that IES was initiated at the time when L-NNA was given and continued until the end of the experiment. In session 2, IES was performed using the proximal pair of serosal electrodes, whereas in session 3, IES was conducted via a pair of intraluminal ring electrodes attached to the tip of the manometric catheter that was inserted into the small intestine via the proximal cannula. The control session was identical to the L-NNA session except the replacement of L-NNA with saline. IES was performed using following parameters (pulse trains): train on-time of 0.5 s and off-time of 2.5 s, pulse frequency of 20 Hz, pulse width of 2 ms, and amplitude of 4 mA. Intestinal transit was measured in the same dogs using a 10-ml solution of phenol red (0.5 mg/ml) mixed with 1.5% methylcellulose was injected into the intestine (distal direction) through the proximal intestine cannula for the assessment of intestinal transit.

Results: The motility index was 9.0±0.8 in the control session and increased to 21.0±2.3 (P=0.001) after L-NNA. The corresponding intestinal transit time was increased from 31.7±6.1 minutes in the control session to 49.0±6.2 minutes with L-NNA (P=0.003). Serosal and intraluminal IES reduced intestine dysmotility and accelerated intestinal transit. The motility index was reduced from 21.0±2.3 in the L-NNA session to 15.1±1.6 during intraluminal IES (P=0.004) and 14±2.4 during serosal IES (P=0.001). No difference was noted in the motility index between intraluminal IES and serosal IES (P=0.28). Interestingly, both intraluminal and serosal IES accelerated small intestine transit. The intestinal transit time was reduced from 49.0±6.2 min in the L-NNA session to 17.7±3.4 min in the intraluminal IES session (P=0.006) and 27.5±6.3 min in the serosal IES session (P=0.02). These values with IES were comparable to that in the control session, suggesting a normalization of intestinal transit. No significant difference was noted between serosal IES and intraluminal IES.

All patents, patent applications, and published references cited herein are hereby incorporated by reference in their entirety. While the devices and methods of the present disclosure have been described in connection with the specific embodiments thereof, it will be understood that they are capable of further modification. Furthermore, this application is intended to cover any variations, uses, or adaptations of the devices and methods of the present disclosure, including such departures from the present disclosure as come within known or customary practice in the art to which the devices and methods of the present disclosure pertain, and as fall within the scope of the appended claims.

What is claimed is:

1. A system for relieving ileus comprising:
   an intraluminal catheter comprising:
      a catheter body having a proximal tip and a distal tip and a duodenal portion proximal to the distal tip of the catheter, the duodenal portion is being configured for placement into a duodenum of a patient;
      a plurality of stimulation electrode pairs disposed along the duodenal portion of the catheter and being configured to provide stimulation energy to the patient;
      a sensing electrode pair disposed on the duodenal portion of the catheter proximally to the plurality of stimulation electrode pairs, the sensing electrode pair is being configured to detect a sensing information comprising an electric signal indicative of intrinsic myoelectric activity of the duodenum of the patient;
      wherein each of the stimulation electrode pairs and the sensing electrode pair comprises two electrodes separated in a longitudinal direction of the catheter by about 3 to about 15 mm, and
      wherein a distance in the longitudinal direction between adjacent electrode pairs is between about 1 cm and about to 10 cm;
   a sensing system in communication with the sensing electrode pair to receive the sensing information; and
   an energy delivery system in communication with the plurality of stimulation electrode pairs and the sensing system, the energy delivery system being configured to deliver stimulation energy to the patient through the plurality of stimulation electrode pairs based on the intrinsic myoelectric activity of the duodenum.

2. The system of claim 1 wherein the energy delivery system is configured to deliver a single pulse of 100 msec at 4 mA in phase with natural electrical activity.

3. The system of claim 1 wherein the energy delivery system is configured to deliver a pulse train of 20 hz at 1-10 mA in phase with natural electrical activity, with a pulse width of 2 msec and duration of 500 msec.

4. The system of claim 1 wherein the energy delivery system is configured to deliver between 12 to 30 pulses per minute out of phase with natural electrical activity, the pulses being of 20 Hz at 4 mA, with a pulse width of 2 msec and duration of 500 msec.

5. The system of claim 1 wherein the catheter further comprises one or more pressure transducers disposed along the duodenal portion.

6. The system of claim 1 wherein the distance in the longitudinal direction between adjacent electrode pairs is between about 3 cm and about to 5 cm.

7. A system for relieving ileus comprising:
an intraluminal catheter comprising:
 a catheter body having a proximal tip and a distal tip and a duodenal portion proximal to the distal tip of the catheter the duodenal portion is being configured for placement into a duodenum of a patient;
 a plurality of sensing electrode pairs disposed along the duodenal portion of the catheter and being configured to detect a sensing information indicative of myoelectric activity of the duodenum of the a patient;
 a plurality of stimulation electrode pairs disposed along the duodenal portion of the catheter and being configured to provide stimulation energy to the patient,
 wherein each stimulation electrode pair and each sensing electrode pair comprises two electrodes separated a longitudinal direction of the catheter by about 3 to about 15 mm; and
 wherein the sensing electrode pairs alternate with the stimulation electrode pairs in the longitudinal direction of the catheter and a distance between adjacent electrode pairs is between about 1 cm and about to 10 cm;
a sensing system in communication with the plurality of sensing electrode pairs to receive the sensing information; and
an energy delivery system in communication with the plurality of stimulation electrode pairs and the sensing system, the energy delivery system being configured to deliver stimulation energy to the patient through the plurality of stimulation electrode pairs based on the intrinsic myoelectric activity of the duodenum.

8. The system of claim 7 wherein sensing electrode pairs are positioned proximally to corresponding stimulation electrode pairs.

9. The system of claim 7 wherein the energy delivery system is configured to deliver a single pulse of 100 msec at 4 mA in phase with natural electrical activity.

10. The system of claim 7 wherein the energy delivery system is configured to deliver a pulse train of 20 hz at 1-10 mA in phase with natural electrical activity, with a pulse width of 2 msec and duration of 500 msec.

11. The system of claim 7 wherein the energy delivery system is configured to deliver between 12 to 30 pulses per minute out of phase with natural electrical activity, the pulses being of 20 Hz at 4 mA, with a pulse width of 2 msec and duration of 500 msec.

12. The system of claim 7 wherein the catheter further comprises one or more pressure transducers disposed along the duodenal portion.

* * * * *